United States Patent

Cooper et al.

[11] Patent Number: 6,043,238
[45] Date of Patent: Mar. 28, 2000

[54] 2-AMINOBENZAZAPINE DERIVATIVES

[75] Inventors: Christopher B. Cooper, Groton; Joseph P. Lyssikatos, Gales Ferry; Donald W. Mann, Voluntown, all of Conn.; Scott J. Hecker, Los Gatos, Calif.

[73] Assignee: Pfizer Inc., New York, N.Y.

[21] Appl. No.: 08/912,091

[22] Filed: Aug. 15, 1997

Related U.S. Application Data

[60] Provisional application No. 60/023,423, Aug. 16, 1996.
[51] Int. Cl.⁷ .......................... C07D 223/16; A61K 31/55
[52] U.S. Cl. .......................... 514/213; 514/215; 514/217; 540/578; 540/580; 540/586; 540/593
[58] Field of Search ...................................... 540/578, 580, 540/586, 593; 514/213, 215, 217

[56] References Cited

U.S. PATENT DOCUMENTS 3,509,130  4/1970  Bencze et al. ........................... 260/239

Primary Examiner—Mukund J. Shah
Assistant Examiner—Brenda Coleman
Attorney, Agent, or Firm—Peter C. Richardson; Paul H. Ginsburg; Jolene W. Appleman

[57] ABSTRACT

A compound of the formula

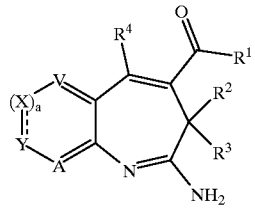

wherein a, V, X, Y, Z, $R^1$, $R^2$, $R^3$ and $R^4$ are as defined above, useful in (a) the treatment of myelosuppression including suppression associated with cancer chemotherapy as well as activation of the immune system for the treatment of cancer or (b) prevention and treatment of viral, fungal, bacterial and parasitic infectious diseases.

5 Claims, No Drawings

2-AMINOBENZAZAPINE DERIVATIVES

This application clims benefit of Provisional Application No. 60/023,423 filed Aug. 16, 1996.

BACKGROUND OF THE INVENTION

The present invention relates to 2-aminobenzazapine derivatives which are immune stimulants with a variety of immunomodulatory activities and as such are useful in the treatment of myelosuppression including suppression associated with cancer chemotherapy as well as activation of the immune system for the treatment of cancer, and in the prevention and treatment of viral, fungal, bacterial and parasitic infectious diseases, either alone or as a vaccine adjunct in conjunction with antimicrobial therapy. This invention also relates to a method of using such compounds in the prevention and treatment of the above diseases in mammals, especially humans, and to the pharmaceutical compositions useful therefor.

The human blood-forming (hematopoietic) system replaces a variety of white blood cells (including neutrophils, macrophages and basophils/mast cells), red blood cells (erythrocytes), and clot-forming cells (megakaryocytes/platelets). The hematopoietic system of the average human male has been estimated to produce on the order of $4.5 \times 10^{11}$ granulocytes and eythrocytes every year, which is equivalent to an annual replacement of total body weight. It is believed that small amounts of certain hematopoietic growth factors account for the differentiation of a small number of progenitor "stem cells" into the variety of blood cell lines for the tremendous proliferation of those lines, and for the ultimate differentiation of mature blood cells from those lines. Granulocyte and Granulocyte-Macrophage Colony Stimulation Factor (G-, and GM-CSF) are two of the four classes of hemopoietic growth factors known as colony stimulating factors (CSF's). GM-CSF is a growth factor which regulates the proliferation and differentiation of multipotential cells. GM-CSF has also been shown to stimulate the formation of clones of neutrophilic granulocytes and mononuclear phagocytic cells from single bone marrow cells in vitro. Colony stimulating factors also activate white blood cells to combat infections of bacteria, fungi, and parasites and accelerate the maturation of leukemic cells, thereby stopping the regeneration of leukemic cells. It is well recognized that human GM-CSF may be useful in the treatment of general hematopoietic disorders including those arising from chemotherapy or from radiation therapy. It may also be useful in bone marrow transplantation. Wound healing, burn treatment, and the treatment of bacterial inflammation may also benefit from the application of human GM-CFS.

In diseases or disease states involving immunosuppression, it is considered invaluable to restore the immune status of an individual in as rapid a fashion as possible to limit the development of opportunistic infections, bacterial, viral, fungal, etc. An agent which would stimulate the production of G or GM-CSF would augment this immunoregulation process.

SUMMARY OF THE INVENTION

The present invention relates to a compound of the formula

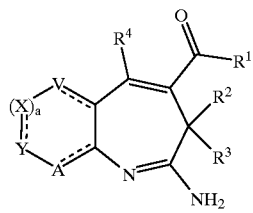

I or the pharmaceutically acceptable salt thereof; wherein the broken lines represent an optional double bonds;

a is 0 or 1;

V, X, Y and Z are each independently oxygen, nitrogen, sulfur or $CR^5$ wherein $R^5$ is hydrogen, $(C_1-C_6)$alkyl optionally substituted by $(C_1-C_6)$alkylamino, $(C_1-C_6)$alkylthio, $(C_1-C_6)$alkoxy, trifluoromethyl, $(C_6-C_{10})$aryl, $(C_5-C_9)$heteroaryl, $(C_6-C_{10})$arylamino, $(C_6-C_{10})$arylthio, $(C_6-C_{10})$aryloxy, $(C_5-C_9)$heteroarylamino, $(C_5-C_9)$heteroarylthio, $(C_5-C_9)$heteroaryloxy, $(C_6-C_{10})$aryl$(C_6-C_{10})$aryl, $(C_3-C_6)$cycloalkyl, hydroxy$(C_1-C_6)$alkyl, $(C_1-C_6)$alkyl (hydroxymethylene), piperazinyl, $(C_6-C_{10})$aryl$(C_1-C_6)$alkoxy, $(C_5-C_9)$heteroaryl$(C_1-C_6)$alkoxy, $(C_1-C_6)$acylamino, $(C_1-C_6)$acylthio, $(C_1-C_6)$acyloxy, $(C_1-C_6)$alkylsulfinyl, $(C_6-C_{10})$arylsulfinyl, $(C_1-C_6)$alkylsulfonyl, $(C_6-C_{10})$arylsulfonyl, amino, $(C_1-C_6)$alkylamino or $((C_1-C_6)$alkyl$)_2$amino; halo, cyano, amino, hydroxy, $(C_2-C_6)$alkenyl, $(C_6-C_{10})$aryl$(C_2-C_6)$alkenyl, $(C_5-C_9)$heteroaryl$(C_2-C_6)$alkenyl, $(C_2-C_6)$alkynyl, $(C_6-C_{10})$aryl$(C_2-C_6)$alkynyl, $(C_5-C_9)$heteroaryl$(C_2-C_6)$alkynyl, $(C_1-C_6)$alkylamino, $((C_1-C_6)$alkyl$)_2$amino, $(C_1-C_6)$alkylsulfonamido, aminosulfonyl, $(C_1-C_6)$alkylaminosulfonyl, $((C_1-C_6)$alkyl$)_2$-aminosulfonyl, $(C_1-C_6)$alkylthio, $(C_1-C_6)$alkoxy, trifluoromethyl, $(C_1-C_6)$alkyl (difluoromethylene), $(C_1-C_3)$alkyl(difluoromethylene) $(C_1-C_3)$alkyl, $(C_6-C_{10})$aryl, $(C_5-C_9)$heteroaryl, $(C_6-C_{10})$arylamino, $(C_6-C_{10})$arylthio, $(C_6-C_{10})$aryloxy, $(C_5-C_9)$heteroarylamino, $(C_5-C_9)$heteroarylthio, $(C_5-C_9)$heteroaryloxy, $(C_3-C_6)$cycloalkyl, $(C_1-C_6)$alkyl(hydroxymethylene), piperidyl, $(C_1-C_6)$alkylpiperidyl, $(C_1-C_6)$acylamino, $(C_1-C_6)$acylthio, $(C_1-C_6)$acyloxy, $R^6(C_1-C_6)$alkyl wherein $R^6$ is $(C_1-C_6)$acylpiperazino, $(C_6-C_{10})$arylpiperazino, $(C_5-C_9)$heteroarylpiperazino, $(C_1-C_6)$alkylpiperazino, $(C_6-C_{10})$aryl$(C_1-C_6)$alkylpiperazino, $(C_5-C_9)$heteroaryl$(C_1-C_6)$alkylpiperazino, morpholino, thiomorpholino, piperidino, pyrrolidino, piperidyl, $(C_1-C_6)$alkylpiperidyl, $(C_6-C_{10})$arylpiperidyl, $(C_5-C_9)$heteroarylpiperidyl, $(C_1-C_6)$alkylpiperidyl$(C_1-C_6)$alkyl, $(C_6-C_{10})$arylpiperidyl$(C_1-C_6)$alkyl, $(C_5-C_9)$heteroarylpiperidyl$(C_1-C_6)$alkyl or $(C_1-C_6)$acylpiperidyl;

or a group of the formula

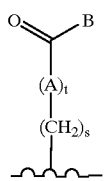

wherein s is 0 to 6;

t is 0 or 1;

A is oxygen or NH;

B is hydroxy, $(C_1-C_6)$alkoxy or $NR^7R^8$ wherein $R^7$ and $R^8$ are each independently hydrogen, $(C_1-C_6)$alkyl optionally substituted by $(C_1-C_6)$alkylpiperidyl, $(C_6-C_{10})$arylpiperidyl, $(C_5-C_9)$heteroarylpiperidyl, $(C_6-C_{10})$aryl, $(C_5-C_9)$heteroaryl, $(C_6-C_{10})$aryl$(C_6-C_{10})$aryl or $(C_3-C_6)$cycloalkyl; piperidyl, $(C_1-C_6)$alkylpiperidyl, $(C_6-C_{10})$arylpiperidyl, $(C_5-C_9)$heteroarylpiperidyl, $(C_1-C_6)$acylpiperidyl, $(C_6-C_{10})$aryl, $(C_5-C_9)$heteroaryl, $(C_6-C_{10})$aryl$(C_6-C_{10})$aryl, $(C_3-C_6)$cycloalkyl, $R^9(C_2-C_6)$alkyl, $(C_1-C_5)$alkyl$(CHR^9)(C_1-C_6)$alkyl wherein $R^9$ is hydroxy, $(C_1-C_6)$acyloxy, $(C_1-C_6)$alkoxy, piperazino, $(C_1-C_6)$acylamino, $(C_1-C_6)$alkylthio, $(C_6-C_{10})$arylthio, $(C_1-C_6)$alkylsulfinyl, $(C_6-C_{10})$arylsulfinyl, $(C_1-C_6)$alkylsulfoxyl, $(C_6-C_{10})$arylsulfoxyl, amino, $(C_1-C_6)$alkylamino, $((C_1-C_6)$alkyl$)_2$amino, $(C_1-C_6)$acylpiperazino, $(C_1-C_6)$alkylpiperazino, $(C_6-C_{10})$aryl$(C_1-C_6)$alkylpiperazino, $(C_5-C_9)$heteroaryl$(C_1-C_6)$alkylpiperazino, morpholino, thiomorpholino, piperidino or pyrrolidino; $R^{10}(C_1-C_6)$alkyl, $(C_1-C_5)$alkyl$(CHR^{10})(C_1-C_6)$alkyl wherein $R^{10}$ is piperidyl or $(C_1-C_6)$alkylpiperidyl; and $CH(R^{11})COR^{12}$ wherein $R^{11}$ is hydrogen, $(C_1-C_6)$alkyl, $(C_6-C_{10})$aryl$(C_1-C_6)$alkyl, $(C_5-C_9)$heteroaryl$(C_1-C_6)$alkyl, $(C_1-C_6)$alkylthio$(C_1-C_6)$alkyl, $(C_6-C_{10})$arylthio$(C_1-C_6)$alkyl, $(C_1-C_6)$alkylsulfinyl$(C_1-C_6)$alkyl, $(C_6-C_{10})$arylsulfinyl$(C_1-C_6)$alkyl, $(C_1-C_6)$alkylsulfonyl$(C_1-C_6)$alkyl, $(C_6-C_{10})$arylsulfonyl$(C_1-C_6)$alkyl, hydroxy$(C_1-C_6)$alkyl, amino$(C_1-C_6)$alkyl, $(C_1-C_6)$alkylamino$(C_1-C_6)$alkyl, $((C_1-C_6)$alkylamino$)_2(C_1-C_6)$alkyl, $R^{13}R^{14}NCO(C_1-C_6)$alkyl or $R^{13}OCO(C_1-C_6)$alkyl wherein $R^{13}$ and $R^{14}$ are each independently hydrogen, $(C_1-C_6)$alkyl, $(C_6-C_{10})$aryl$(C_1-C_6)$alkyl or $(C_5-C_9)$heteroaryl$(C_1-C_6)$alkyl; and $R^{12}$ is $R^{15}O$ or $R^{15}R^{16}N$ wherein $R^{15}$ and $R^{16}$ are each independently hydrogen, $(C_1-C_6)$alkyl, $(C_6-C_{10})$aryl$(C_1-C_6)$alkyl or $(C_5-C_9)$heteroaryl$(C_1-C_6)$alkyl;

$R^1$ is hydrogen, hydroxy, $(C_1-C_6)$alkoxy optionally susbstituted by hydroxy; $(C_1-C_6)$alkyl, $(C_6-C_{10})$aryl or $NR^{17}R^{18}$ wherein $R^{17}$ and $R^{15}$ are each independently hydrogen, $(C_1-C_6)$alkyl, piperidyl, $(C_1-C_6)$alkylpiperidyl, $(C_6-C_{10})$arylpiperidyl, $(C_5-C_9)$heteroarylpiperidyl, $(C_6-C_{10})$aryl$(C_1-C_6)$alkylpiperidyl, $(C_5-C_9)$heteroaryl$(C_1-C_6)$alkylpiperidyl, $(C_1-C_6)$acylpiperidyl, $(C_6-C_{10})$aryl, $(C_5-C_9)$heteroaryl, $(C_6-C_{10})$aryl$(C_1-C_6)$alkyl, $(C_5-C_9)$heteroaryl$(C_1-C_6)$alkyl, $(C_6-C_{10})$aryl$(C_6-C_{10})$aryl, $(C_6-C_{10})$aryl$(C_6-C_{10})$aryl$(C_1-C_6)$alkyl, $(C_3-C_6)$cycloalkyl, $(C_3-C_6)$cycloalkyl$(C_1-C_6)$alkyl, $R^{19}(C_2-C_6)$alkyl, $(C_1-C_6)$alkyl$(CHR^{19})(C_1-C_6)$alkyl wherein $R^{19}$ is hydroxy, $(C_1-C_6)$acyloxy, $(C_1-C_6)$alkoxy, piperazino, $(C_1-C_6)$acylamino, $(C_1-C_6)$alkylthio, $(C_6-C_{10})$arylthio, $(C_1-C_6)$alkylsulfinyl, $(C_6-C_{10})$arylsulfinyl, $(C_1-C_6)$alkylsulfoxyl, $(C_6-C_{10})$arylsulfoxyl, amino, $(C_1-C_6)$alkylamino, $((C_1-C_6)$alkyl$)_2$ amino, $(C_1-C_6)$acylpiperazino, $(C_1-C_6)$alkylpiperazino, $(C_6-C_{10})$aryl$(C_1-C_6)$alkylpiperazino, $(C_5-C_9)$heteroaryl$(C_1-C_6)$alkylpiperazino, morpholino, thiomorpholino, piperidino or pyrrolidino; $R^{20}(C_1-C_6)$alkyl, $(C_1-C_5)$alkyl$(CHR^{20})(C_1-C_6)$alkyl wherein $R^{20}$ is piperidyl, $(C_1-C_6)$alkylpiperidyl, $(C_6-C_{10})$arylpiperidyl, $(C_6-C_{10})$aryl$(C_1-C_6)$alkylpiperidyl, $(C_5-C_9)$heteroarylpiperidyl or $(C_5-C_9)$heteroaryl$(C_1-C_6)$alkylpiperidyl; and $CH(R^{21})COR^{22}$ wherein $R^{21}$ is hydrogen, $(C_1-C_6)$alkyl, $(C_6-C_{10})$aryl$(C_1-C_6)$alkyl, $(C_5-C_9)$heteroaryl$(C_1-C_6)$alkyl, $(C_1-C_6)$alkylthio$(C_1-C_6)$alkyl, $(C_6-C_{10})$arylthio$(C_1-C_6)$alkyl, $(C_1-C_6)$alkylsulfinyl$(C_1-C_6)$alkyl, $(C_6-C_{10})$arylsulfinyl$(C_1-C_6)$alkyl, $(C_1-C_6)$alkylsulfonyl$(C_1-C_6)$alkyl, $(C_6-C_{10})$arylsulfonyl$(C_1-C_6)$alkyl, hydroxy$(C_1-C_6)$alkyl, amino$(C_1-C_6)$alkyl, $(C_1-C_6)$alkylamino$(C_1-C_6)$alkyl, $((C_1-C_6)$alkylamino$)_2(C_1-C_6)$alkyl, $R^{23}R^{24}NCO(C_1-C_6)$alkyl or $R^{23}OCO(C_1-C_6)$alkyl wherein $R^{23}$ and $R^{24}$ are each independently hydrogen, $(C_1-C_6)$alkyl, $(C_6-C_{10})$aryl$(C_1-C_6)$alkyl or $(C_5-C_9)$heteroaryl$(C_1-C_6)$alkyl; and $R^{22}$ is $R^{25}O$ or $R^{25}R^{26}N$ wherein $R^{25}$ and $R^{26}$ are each independently hydrogen, $(C_1-C_6)$alkyl, $(C_6-C_{10})$aryl$(C_1-C_6)$alkyl or $(C_5-C_9)$heteroaryl$(C_1-C_6)$alkyl;

or $R^{17}$ and $R^{18}$, or $R^{23}$ and $R^{24}$, or $R^{25}$ and $R^{26}$ may be taken together to form azetidinyl, pyrrolidinyl, piperidinyl, morpholinyl, thiomorpholinyl, indolinyl, isoindolinyl, tetrahydroquinolinyl, tetrahydroisoquinolinyl, $(C_1-C_6)$acylpiperazinyl, $(C_1-C_6)$alkylpiperazinyl, $(C_6-C_{10})$arylpiperazinyl, $(C_5-C_9)$heteroarylpiperazinyl wherein each heterocyclic group may be substituted by carboxy, amino, $(C_1-C_6)$alkyl, $(C_6-C_{10})$aryl, $(C_5-C_9)$heteroaryl, $NHR^{27}$, $NR^{27}R^{28}$, $NHSO_2R^{29}$, $CHR^{27}R^{28}$, $SO_2R$ or $SO_2R^{27}R^{28}$ wherein $R^{27}$, $R^{28}$ and $R^{29}$ are each independently hydrogen, $(C_1-C_6)$alkyl, $(C_6-C_{10})$aryl, $(C_5-C_9)$heteroaryl, $(C_6-C_{10})$aryl$(C_1-C_6)$alkyl or $(C_5-C_9)$heteroaryl$(C_1-C_6)$alkyl; or a bridged diazabicycloalkyl ring selected from the group consisting of

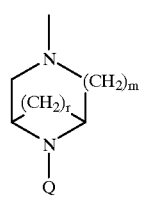

a

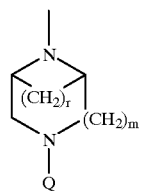

b

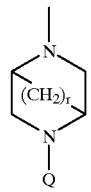

c

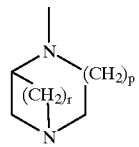

d

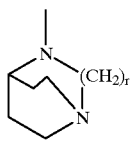

wherein r is 1, 2 or 3;
m is 1 or 2;
p is 0 or 1;and
Q is hydrogen, $(C_1-C_3)$alkyl or $(C_1-C_6)$acyl; and
$R^2$, $R^3$ and $R^4$ are each independently hydrogen, $(C_1-C_6)$ alkyl, $(C_1-C_6)$alkoxy, hydroxy, hydroxy$(C_1-C_6)$alkyl, hydroxy $(C_1-C_6)$alkoxy or $NR^6R^7$ wherein $R^6$ and $R^7$ are each independently hydrogen, $(C_1-C_6)$alkyl or $(C_1-C_6)$alkoxy;
or when a is 1 and X and Y are both $CR^5$, the two $R^5$ groups may be taken together with the adjacent carbons to which they are attached to form a 1,3-dioxolyl group, pyrrolyl group optionally susbtituted by one or two nitro, $(C_1-C_6)$alkyl or $(C_1-C_6)$alkoxy groups; or a compound of the formula

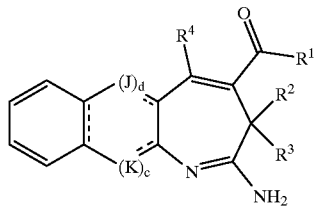

XV wherein the broken lines represent optional double bonds;
$R^1$, $R^2$, $R^3$ and $R^4$ are as defined above;
c is 0 or 1;
d is 0 or 1; and
J and K are each independently NH or $CR^{30}$ wherein $R^{30}$ is hydrogen, $(C_1-C_6)$alkyl or $(C_1-C_6)$alkoxy;
with the proviso that the sum of c and d cannot be 0;
with the proviso that when V is oxygen or sulfur and a is 1, X is nitrogen or $CR^5$;
with the proviso that when V is oxygen or sulfur and a is 0, Y is nitrogen or $CR^5$;
with the proviso that when a is 1 and X is oxygen or sulfur, V and Y are both independently nitrogen or $CR^5$;
with the proviso that when Y is oxygen or sulfur and a is 1, X and Z are both independently nitrogen or $CR^5$;
with the proviso that when Y is oxygen or sulfur and a is 0, V and Z are both independently nitrogen or $CR^5$; and
with the proviso that when Z is oxygen or sulfur, Y is nitrogen or $CR^5$.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined above.

The term "aryl", as used herein, unless otherwise indicated, includes an organic radical derived from an aromatic hydrocarbon by removal of one hydrogen, such as phenyl or naphthyl, optionally substituted by 1 to 3 substituents selected from the group consisting of fluoro, chloro, trifluoromethyl, $(C_1-C_6)$alkoxy, $(C_6-C_{10})$aryloxy, trifluoromethoxy, difluoromethoxy and $(C_1-C_6)$alkyl.

The term "heteroaryl", as used herein, unless otherwise indicated, includes an organic radical derived from an aromatic heterocyclic compound by removal of one hydrogen, such as pyridyl, furyl, pyroyl, thienyl, isothiazolyl, imidazolyl, benzazapinyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl, optionally substituted by 1 to 2 substituents selected from the group consisting of fluoro, chloro, trifluoromethyl, $(C_1-C_6)$alkoxy, $(C_6-C_{10})$aryloxy, trifluoromethoxy, difluoromethoxy and $(C_1-C_6)$alkyl.

The term "acyl", as used herein, unless otherwise indicated, includes a radical of the general formula RCO wherein R is alkyl, alkoxy, aryl, arylalkyl or arylalkyloxy and the terms "alkyl" or "aryl" are as defined above.

The term "acyloxy", as used herein, includes O-acyl groups wherein "acyl" is defined above.

The compound of formula I may have chiral centers and therefore exist in different enantiomeric forms. This invention relates to all optical isomers and stereoisomers of the compounds of formula I and mixtures thereof.

Preferred compounds of formula I include those wherein $R^1$ is hydrogen, hydroxy, $(C_1-C_6)$alkoxy optionally substituted by hydroxy; $(C_1-C_6)$alkyl, $(C_6-C_{10})$aryl or $NR^{17}R^{18}$ wherein $R^{17}$ and $R^{18}$ are each independently hydrogen, $(C_1-C_6)$alkyl, $(C_1-C_6)$alkoxy or $(C_6-C_{10})$aryl; or $R^{17}$ and $R^{18}$ may be taken together with the nitrogen to which they are attached to form a pyrrolidinyl or piperidinyl ring.

Other preferred compounds of formula I include those wherein $R^2$, $R^3$ and $R^4$ are each hydrogen.

Other preferred compounds of formula I include those wherein a is 1; V, X, Y and Z are each $CR^5$ wherein each $R^5$ is independently selected from hydrogen, halo, cyano, hydroxy, $((C_1-C_6)$alkyl$)_2$amino, trifluoromethyl, or a group of the formula

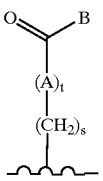

wherein s is 0; t is 0; and B is $(C_1-C_6)$alkoxy or $NR^7R^8$ wherein $R^7$ and $R^8$ are each $(C_1-C_6)$alkyl.

More preferred compounds of formula I include those wherein $R^1$ is hydrogen, hydroxy, $(C_1-C_6)$alkoxy optionally substituted by hydroxy; $(C_1-C_6)$alkyl, $(C_6-C_{10})$aryl or $NR^7R^{18}$ wherein $R^{17}$ and $R^{18}$ are each independently hydrogen, $(C_1-C_6)$alkyl, $(C_1-C_6)$alkoxy or $(C_6-C_{10})$aryl; or $R^{17}$ and $R^{18}$ may be taken together with the nitrogen to which they are attached to form a pyrrolidinyl or piperidinyl ring; $R^2$, $R^3$ and $R^4$ are each hydrogen; a is 1; and V, X, Y and Z are each $CR^5$ wherein each $R^5$ is independently selected from hydrogen, halo, cyano, hydroxy, $((C_1-C_6)$alkyl$)_2$amino, trifluoromethyl, or a group of the formula

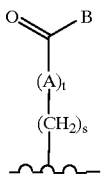

wherein s is 0; t is 0; and B is $(C_1-C_6)$alkoxy or $NR^7R^8$ wherein $R^7$ and $R^8$ are each $(C_1-C_6)$alkyl.

Specific preferred compounds of formula I include the following;

2-Amino-8-hydroxy-9-methoxy-3H-benzo[b]azepine-4-carboxylic acid ethyl ester;
2-Amino-9-methoxy-3H-benzo[b]azepine-4-carboxylic acid ethyl ester;
2-Amino-7-hydroxy-8-methoxy-3H-benzo[b]azepine-4-carboxylic acid ethyl ester;
2-Amino-6-methoxy-3H-benzo[b]azepine-4-carboxylic acid ethyl ester;
6-Amino-7H-1,3-dioxa-5-aza-cyclohepta[f]indene-8-phenyl)-propionic acid methyl ester;
8-Acetyl-2-amino-3H-benzo[b]azepine-4-carboxylic acid ethyl ester;
8-acetyl-2-amino-3H-benzo[b]azepine-4-carboxylic acid dipropylamide;
2-Amino-8-hydroxy-7-methoxy-3H-benzo[b]azepine-4-carboxylic acid ethyl ester;
2-[(2-Amino-3H-benzo[b]azepine-4-carbonyl)-amino]-propionic acid methyl ester;
2-[(2-Amino-3H-benzo[b]azepine-carbonyl)-amino]-propionic acid benzyl ester;
2-[(2-Amino-3H-benzo[b]azepine-4-carbonyl)-amino]-3-methyl-butyric acid methyl ester; and
2-Amino-3H-benzo[b]azepine-4-carbaldehyde.

The present invention also relates to a pharmaceutical composition for (a) the treatment of myelosuppression including suppression associated with cancer chemotherapy as well as activation of the immune system for the treatment of cancer or (b) prevention or treatment of viral, fungal, bacterial and parasitic infectious diseases in a mammal, including a human, comprising an amount of a compound of formula I or a pharmaceutically acceptable sale thereof, effective in such prevention or treatment and a pharmaceutically acceptable carrier.

The present invention also relates to a method for (a) the treatment of myelosuppression including suppression associated with cancer chemotherapy as well as activation of the immune system for the treatment of cancer or (b) prevention or treatment of viral, fungal, bacterial and parasitic infectious diseases in a mammal, including a human, comprising administering to said mammal an amount of a compound of formula I or a pharmaceutically acceptable salt thereof, effective in such prevention or treatment.

DETAILED DESCRIPTION OF THE INVENTION

The following reaction Schemes illustrate the preparation of compounds of the present invention. Unless otherwise indicated a, V, X, Y, Z, $R^2$, $R^3$, $R^4$, $R^{17}$ and $R^{18}$ in the reaction Schemes and the discussion that follow are defined as above.

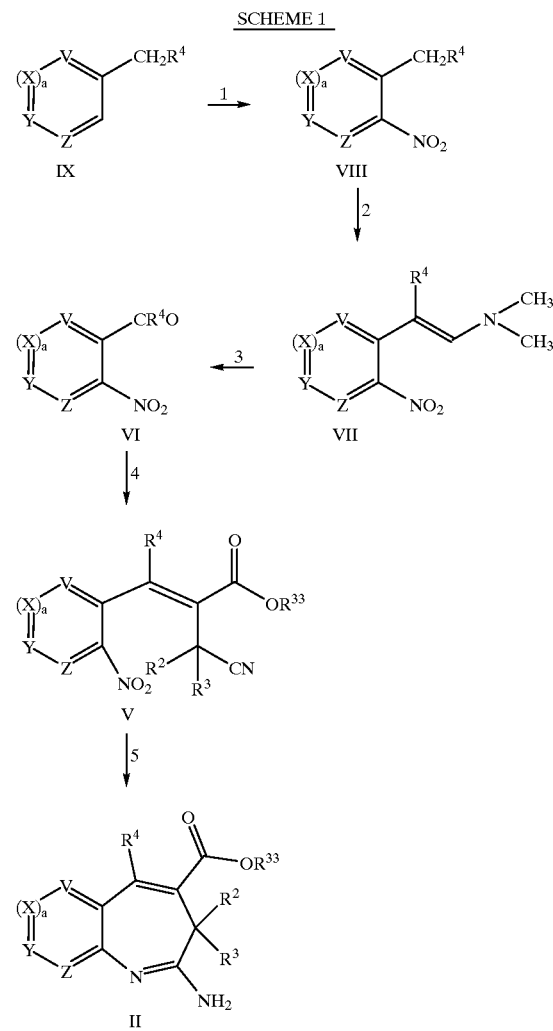

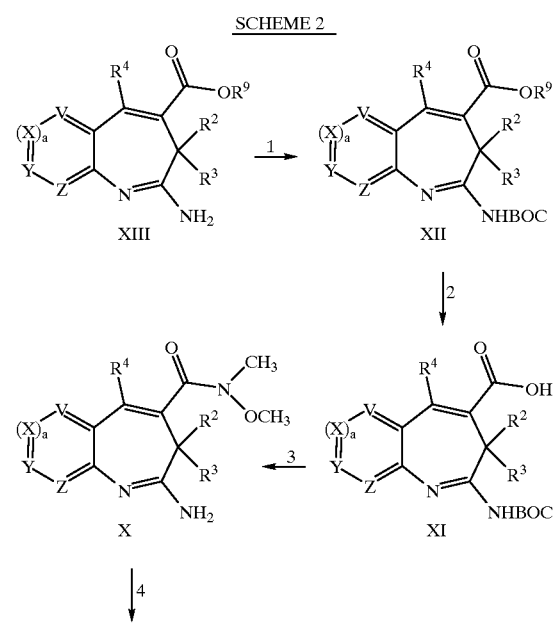

-continued

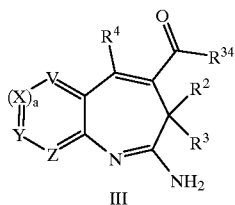
III

SCHEME 3

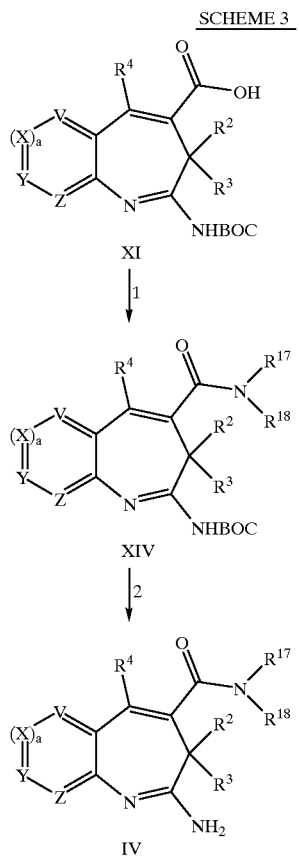

SCHEME 4

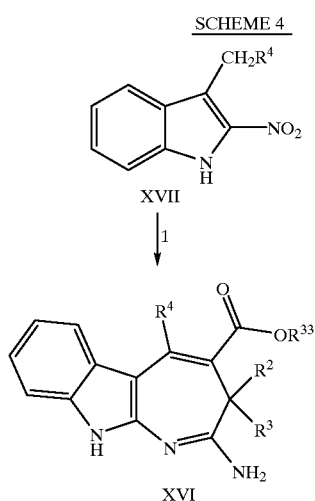

SCHEME 5

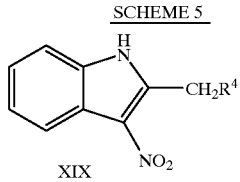
XIX

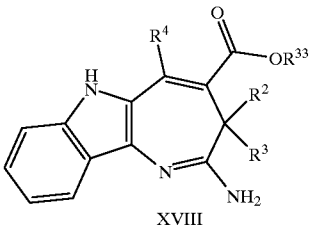
XVIII

In reaction 1 of Scheme 1, the compound of formula IX is converted to the corresponding 2-nitrotoluene compound of formula VIII by adding 1,4-dioxane to a suspension of IX in concentrated sulfuric acid. The solution so formed is cooled to a temperature between about −5° C. to about 10° C., preferably about 0° C., and nitric acid is then added dropwise. The resulting reaction mixture is warm to room temperature and allowed to stir for a time period between about 10 hours to about 14 hours, preferably about 12 hours.

In reaction 2 of Scheme 1, the compound of formula VIII is converted to the corresponding compound of formula VII by reacting VIII with N,N-dimethylformamide dimethyl acetal in a polar aprotic solvent, such as dimethylformamide. The reaction mixture is heated, under an inert atmosphere, to a temperature between about 130° C. to about 150° C., preferably about 140° C., for a time period between about 10 hours to about 14 hours, preferably about 12 hours.

In reaction 3 of Scheme 1, the compound of formula VII is converted to the corresponding 2-nitrobenzaldehyde compound of formula VI by oxidizing VII with sodium periodate in a 1:1 ratio solution of aqueous tetrahydrofuran. The reaction mixture is stirred, at room temperature, for a time period between about 15 minutes to about 1 hour, preferably about 30 minutes.

In reaction 4 of Scheme 1, the compound of formula VI is converted to the corresponding compound of formula V by reacting, under an inert atmosphere, VI with an ylide of the formula

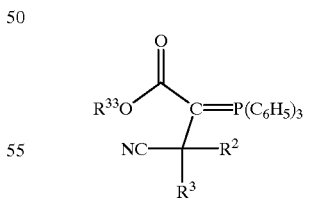

wherein $R^{33}$ is hydrogen, $(C_1-C_6)$alkyl or hydroxy$(C_1-C_6)$alkyl, in a polar aprotic solvent, such as toluene. The reaction mixture is heated to reflux and stirred for a time period between about 4 hours to about 6 hours, preferably about 5 hours.

In reaction 5 of Scheme 1, the compound of formula V is converted to the corresponding 2-aminobenzazapine compound of formula II by heating V in the presence of iron power and a polar protic solvent, such as AcOH, to a temperature between about 65° C. to about 95° C., preferably about 80° C. The reaction mixture is stirred, under an inert atmosphere, for a time period between about 1 0 hours to about 14 hours, preferably about 12 hours.

In reaction 1 of Scheme 2, the 2-aminobenzazapine compound of formula XIII, wherein $R^9$ is $(C_1-C_6)$alkyl, is converted to the corresponding compound of formula XII by reacting XIII with N-tert-butoxycarbonyl anhydride in a polar aprotic solvent, such as methylene chloride. The reaction mixture is stirred, at room temperature, for a time period between about 10 hours to about 14 hours, preferably about 12 hours.

In reaction 2 of Scheme 2, the compound of formula XII is converted to the corresponding carboxylic acid compound of formula XI by reacting XII with lithium hydroxide in a polar solvent, such as aqueous tetrahydrofuran. The reaction mixture is stirred at a temperature between about 60° C. to about 90° C., preferably about 75° C., for a time period between about 1 hour to about 3 hours, preferably about 2 hours.

In reaction 3 of Scheme 2, the compound of formula XI is converted to the corresponding amide compound of formula X by adding a solution of XI in a polar aprotic solvent, such as dimethyl formamide, to a solution of N,O-dimethylhydroxylamine hydrochloride and a base, such as triethylamine, in a polar protic solvent, such as dimethyl formamide. Diethyl pyrocarbonate is then added to the resulting solution. The reaction mixture so formed is stirred, at room temperature, for a time period between about 10 minutes to about 30 minutes, preferably about 20 minutes.

In reaction 4 of Scheme 2, the compound of formula X is converted to the corresponding 2-aminobenzazapine compound of formula III, wherein $R^{34}$ is $(C_1-C_6)$alkyl or hydroxy$(C_1-C_6)$alkyl, by reacting, under an inert atmosphere, a solution of X in a polar aprotic solvent, such as tetrahydrofuran, cooled to a temperature between about −90° C. to about −70° C., preferably about −780° C., with an alkyl lithium. After approximately 10 minutes, the reaction mixture so formed is allowed to warm to room temperature, quenched with hydrochloric acid and stirred for a time period between about 30 minutes to about 1 hour, preferably about 45 minutes.

In reaction 1 of Scheme 3, the carboxylic acid compound of formula XI is converted to the corresponding amide compound of formula XIV by reacting XI with $R^{17}R^{18}$amine, diethyl pyrocarbonate and triethylamine in a polar aprotic solvent, such as methylene chloride. The reaction mixture was stirred, at room temperature, for a time period between about 6 hours to about 8 hours, preferably about 7 hours.

In reaction 2 of Scheme 3, the compound of formula XIV is converted to the corresponding 2-aminobenzazapine compound of formula IV by treating XIV with hydrochloric acid in a aprotic solvent, such as dioxane, or with trifluoracetic acid neat at a temperature between about −30° C. to about 70° C., preferably about −5° C. to about 35° C.

In reaction 1 of Scheme 4, the 2-nitroindole compound of formula XVII is converted to the corresponding compound of formula XVI according to the procedure described above in reactions 2, 3, 4 and 5 of Scheme 1.

In reaction 1 of Scheme 5, the 3-nitroindole compound of formula XIX is converted to the corresponding compound of formula XVIII according to the procedure described above in reactions 2, 3, 4 and 5 of Scheme 1.

Biological Assay

In vitro Bone Marrow Proliferation

Bovine sternum bone marrow marrow is placed into a sterile sieve which sits in the bottom of a Petrie dish. The contents are mashed with a glass pestle. Alsevers solution is then poured over the contents to rinse and release cells. The liquid from the Petrie dish is collected (single cell suspension) and transfered to a bottle. The contents of the Petrie dish are mashed and rinsed again.

The cell suspension is filtered through sterile nylon mesh into 50 ml conical centrifuge tubes. Centrifuge at 1200 rpm (approximately 300 g) for 10 minutes. Discard supernatant. Resuspend in Alsevers solution and wash two more times. Count nucleated blood cells on Coulter counter (model ZM) using zapoglobin for pre-gradient concentration.

Set up ficoll gradients using 20 ml of 1.077 histopaque at room temperature in 50 ml tubes. Layer 20–30 ml of bone marrow suspension at a concentration range of 1 to $3 \times 10^{-9}$ white blood cells/gradient. Spin gradients at 1400 rpm (approximately 450 g) for 30 minutes at room temperature with centrifuge brake OFF.

Remove and discard supernatant. Carefully collect white blood cells layer at interface from each tube and pool (including red blood cells is unavoidable-nucleated red blood cells do not clearly separate from white blood cell's. Bring up to 50 ml with Alsevers solution.

Count white blood cells for gradient yield (typically 10–15%). Wash two more times in Alsevers solution, spinning at 1000 rpm (approximately 225 g) 10 minutes. Check platelet-to-cell ratio using the Coulter counter. Cells should outnumber platelets in a ratio of at least 2 to 1. Then wash once in Serum-Free RPMI and obtain final concentration and culture at 50,000 cells per well in 96-well microtiter plates using a volume of 150 ul.

Compound preparation: synthetic compounds are dissolved as a 1 mg/ml working stock in Serum-Free RPMI +10% dimethyl sulfoxide. Note: Add dimethyl sulfoxide first, solubilize compound, then add medium. Dilute appropriately to run compounds starting at 1.0 ug/ml with 3-fold dilutions. Typically compounds are diluted to 4 times stocks and 50 ul are added to wells containing 150 ul cell suspension. Plates are incubated at 39° C. in 5% carbon dioxide for 4 days.

Tritiated thymidine is added to each well at a final concentration of 2 uCi/ml. 3H-thymidine is purchased as a 1 mCi/ml stock, dilute to 20 uCi/ml with Serum-Free RPMI, then add to wells as a 10% volume, i.e., 22 ul is added to the 200 ul volume now in wells. Incubate plates at 39° C. in 5% carbon dioxide for approximately 18 hours more.

At the end of the labeling period freeze the plates. Thaw plates just before harvesting and harvest cells on glass fiber 96-well filtermats. Use a Betaplate scintillation counter for 1 minute counts.

Calculate activity by dividing the counts per minute of the sample by the medium control for fold-over-background. Activity of 3 or more fold-over background is considered positive.

For administration to mammals, including humans, a variety of conventional routes may be used including orally, parenterally and topically. In general, the active compound will be administered orally or parenterally at dosages between about 0.1 and 25 mg/kg body weight of the subject to be treated per day, preferably from about 0.3 to 5 mg/kg. However, some variation in dosage will necessarily occur depending on the condition of the subject being treated. The person responsible for administration will, in any event, determine the appropriate dose for the individual subject.

The compounds of the present invention can be administered in a wide variety of different dosage forms. In general, the compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof. In the case of animals, they are advantageously contained in an animal feed or drinking water in a concentration of 5–5000 ppm, preferably 25 to 500 ppm.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. In the case of animals, compounds can be administered intramuscularly or subcutaneously at dosage levels of about 0.1 to 50 mg/kg/day, advantageously 0.2 to 10 mg/kg/day given in a single dose or up to 3 divided doses.

The present invention is illustrated by the following examples, but it is not limited to the details thereof.

EXAMPLE 1

2-Amino-7-fluoro-3H-benzo[b]azepine-4-carboxylic Acid Ethyl Ester 1,4 Dioxane was slowly added to a suspension of 4-fluorotoluene (6.6 grams, 34.7 mmol) in 30 ml concentrated sulfuric acid until the suspension began to become soluble (6 ml). The reaction was cooled to 0° C. and nitric acid (5.6 grams, 85.3 mmol) was slowly added. The reaction gradually became yellow over time. The reaction was allowed to warm to room temperature overnight, and then worked up by pouring over ice and water. This solution was extracted repeatedly with ethyl acetate. Organics were washed with several portions of water, dried over magnesium sulfate and concentrated in vacuo to yield 6.8 grams of a yellow-orange oil (86%).

To a flame dried 65 ml roundbottom was added 20 ml of and anhydrous N,N-dimethylformamide, 2.94 gm (24.7 mmol) of N,N-dimethylformamide-dimethyl acetal and 3.00 grams (19.3 mmol) of 4-fluoro-2-nitrotoluene. The reaction was heated overnight at 140° C. under nitrogen. The solution was concentrated in vacuo to give a red oil. Upon dilution with cold methanol, red crystals precipitated to give 2.65 grams (65% yield).

500 mg (2.37 mmol) of the above enamine was dissolved in 50 ml of a 1:1 solution of aqueous tetrahydrofuran and 1.53 grams (7.14 mmol) of sodium periodate was added. The reaction was stirred for 30 minutes and then filtered. The filtrate was extracted with ethyl acetate and washed with saturated bicarbonate solution then with brine. The organic layer was dried over magnesium sulfate filtered, and concentrated in vacuo to give 345 mg (86% yield) of an orange solid. An analytically pure sample was obtained by recystallization from methanol.

0.313 grams (1.33 mmol) of 4-fluoro-2-nitrobenzaldehyde and 0.482 grams (1.37 mmol) of α-cyanomethylcarboethoxyethylidene triphenylphosphorane were combined and dissolved in 10 ml of anhydrous toluene and stirred under nitrogen. The reaction mixture was heated to reflux with stirring for 10 hours. The reaction was allowed to cool to room temperature overnight. This material was worked up by extracting the resulting solid by the addition of 50 ml of ether twice. The mixture was filtered and the filtrate was concentrated in vacuo to give a tan solid.

440 mg (7.6 mmol) of iron powder was added to a stirring solution of ethyl 4'-fluoro-α-cyanomethylcinnamate (0.457 grams, 1.13 mmol) in 10 ml AcOH. The reaction was then heated to 80° C. and stirred under nitrogen overnight. The reaction was cooled to room temperature, diluted with methylene chloride and filtered. The precipatate was washed with methylene chloride. The filtrate was slowly treated with solid $Na_2CO_3$ until the pH was equal to 9. The layers were separated, and the organic layer was washed with water, brine, and dried over sodium sulfate. The dried filrate was concentrated in vacuo to give 345 mg of a yellow solid. The solid was recrystalized from ethyl acetate/hexanes to give 257 mg (58%) of a white solid.

$^1$H NMR (250MHz, $CD_3OD$ d 7.83 (s, 1H), 7.56 (d, J=8.2 Hz, 1H), 7.39 (s, 1H), 7.26 (d, J=8.2 Hz, 1H), 4.31 (q, J=7.1 Hz, 2H), 3.01 (s, 2H), 1.36 (t, J=8.2 Hz, 3H); Analysis: calcd for C, 56.38;H. 4.39; N, 9.39; found C, 56.22; H, 4.55; N, 9.37.

The title compounds of examples 2–10 were prepared analogously to the title compound described in Example 1 using the starting material indicated.

EXAMPLE 2

2-Amino-7,8-dimethoxy-3H-benzo[b]azepine-4-carboxylic Acid Propyl Ester

Starting material: 3,4-dimethoxytoluene. $^1$H NMR (250 MHz, $CDCl_3$) d 7.74 (s, 1H), 6.81 (s, 1H), 6.75 (s, 1H), 4.84 (br s, 2H), 4.21 (t, J=6.7 Hz, 2H), 3.92 (s, 3H), 3.91 (s, 3H), 2.93 (s, 2H), 1.78 (m, 2H), 1.03 (t, J=7.6 Hz, 3H); $^{13}$C NMR (75.5 MHz, $CDCl_3$) d 166.0, 152.1, 150.6, 144.3, 143.9, 137.9, 120.0, 119.4, 112.2, 109.1, 66.66, 56.01, 55.83, 31.11, 22.13, 10.55; HRMS calcd 304.14229 found 304.14276.

EXAMPLE 3

2-Amino-8-methoxy-3H-benzo[b]azepine-4-carboxylic Acid Ethyl Ester

Starting material: 4-methoxytoluene. $^1$H NMR (300 MHz, $CDCl_3$) d 7.69 (s, 1H), 7.22 (d. J=8.5Hz, 1H), 6.60–6.65 (m, 2H), 5.04 (brs, 1H), 4.22 (q, J=7.1 Hz, 2H), 3.77 (s, 3H), 2.87 (s, 2H), 1.30 (t, J=7.1 Hz, 3H); $^{13}$C NMR (75.5 MHz, CDCl₃) d 165.9, 160.5, 153.4, 150.0, 138.4, 132.8, 120.3, 120.2, 110.6, 109.2, 60.96, 55.19, 31.04, 14.29; HRMS calcd 260.11608 found 260.11745.

EXAMPLE 4

2-Amino-7-methoxy-3H-benzo[b]azepine-4-carboxylic Acid Ethyl Ester

Starting material: 3-methoxytoluene. $^1$H NMR (300 MHz, CDCl₃) d 7.68 (s, 1H), 7.09 (d, J=8.9 Hz, 1H), 6.91 (dd, J=3.0, 8.9 Hz, 1H), 6.78 (d, J=3.0 Hz, 1H), 4.23 (q, J=7.1 Hz, 2H), 3.76 (s, 3H), 2.85 (s, 2H), 1.31 (t, J=7.1 Hz, 3H); FAB MH+ 261.

EXAMPLE 5

2-Amino-7-cyano-3H-benzo[b]azepine-4-carboxylic Acid Ethyl Ester

Starting material: 3-cyanotoluene. $^1$H NMR (300 MHz, CD₃OD) d 8.05 (s, 1H), 7.96 (s, 1H), 7.86 (d, J=8.5 Hz,1H), 7.52 (d, J=8.5 Hz, 1H), 4.34 (q, J=7.1 Hz, 2H), 1.37 (t, J=7.1 Hz, 3H); 13C NMR (75.5 MHz, CD₃OD) d 165.4, 140.2, 138.0, 137.6, 134.6, 129.9, 129.1, 125.5, 118.5, 111.2, 63.24, 30.13, 14.51; HRMS calcd 255.10077; found 255.10465.

EXAMPLE 6

2-Amino-7-methoxy-3H-benzo[b]azepine-4-carboxylic Acid Methyl Ester

Starting material: 3-methoxytoluene. $^1$H NMR (250 MHz, CDCl₃) d 7.76 (s, 1H), 7.17 (d, J=8.9 Hz, 1H), 6.99 (dd, J=3.0, 8.9 Hz, 1H), 6.83 (d, J=3.0 Hz, 1H), 4.97 (brs, 2H), 3.86 (s, 3H), 3.83 (s, 3H), 2.93 (s, 2H); HRMS calcd 246.10043; found 246.09943.

EXAMPLE 7

2-Amino-7-dimethylamino-3H-benzo[b]azepine-4-carboxylic Acid Ethyl Ester

Starting material: 3-N,N-dimethylaminotoluene. $^1$H NMR (250 MHz, CDCl₃) d 7.77 (s, 1H), 7.19 (d, J=9.0 Hz, 1H), 6.92 (dd, J=2.9, 9.0 Hz, 1H), 6.67 (d, J=2.9 Hz, 1H), 4.31 (q, J=7.1Hz, 2H), 2.99 (s, 2H),2.96 (s, 6H), 1.38 (t, J=7.1Hz, 3H); HRMS calcd 273.14772; found 273.14773.

EXAMPLE 8

8-Dimethylamino-2-imino-2,3-dihydro-1H-benzo[b]azepine-4-carboxylic Acid Ethyl Ester Starting material: 4-N,N,-dimethylaminotoluene. $^1$H NMR (250 MHz, CDCl₃) d 7.74 (s, 1H), 7.25 (d, J=8.7 Hz, 1H), 6.53 (dd, J=2.4, 8.7 Hz, 1H), 6.48 (d, J=2.4 Hz, 1H), 4.28 (q, J=7.1 Hz, 2H), 3.02 (s, 6H), 2.96 (s, 2H), 1.38 (t, J=7.1 Hz, 3H); HRMS calcd 273.1477; found 273. 1473.

EXAMPLE 9

2-Amino-7-fluoro-3H-benzo[b]azepine-4-carboxylic Acid Ethyl Ester

Starting material: 3-fluorotoluene. $^1$H NMR (250 MHz, CDCl₃) d 7.72 (s, 1 H), 7.02–7.22 (m, 3H), 4.31 (q, J=7.2 Hz, 2H), 2.93 (s, 2H), 1.39 (t, J=7.2 Hz, 3H); HRMS calcd 248.09610; found 248.09402.

EXAMPLE 10

2-Amino-7,8-dimethoxy-3H-benzo[b]azepine-4-carboxylic Acid Ethyl Ester

Starting material: 3,4-dimethoxytoluene. $^1$H NMR (250 MHz, CDCl₃) d 7.74 (s, 1H), 6.80 (s, 1H), 6.73 (s, 1H), 4.89 (brs 2H), 4.30 (q, J=7.2 Hz, 2H), 3.92 (s, 3H), 3.91 (s, 3H), 2.92 (s, 2H), 1.38 (t, J=7.2 Hz, 3H); MH+ 291.

EXAMPLE 11

1-(2-Amino-3H-benzo[b]azepin-4-yl)-pentan-1-one

Boc-anhydride (2.98 grams, 13.7 mmol) was added to a stirring solution of 2-amino-3H-benzo[b]azepine-4-carboxylic acid ethyl ester (3.003 grams 13.03 mmol) in 65 ml of methylene chloride. The reaction was stirred overnight at room temperature. The reaction mixture was partitioned between IN phosphoric acid and methylene chloride. The organic layer was washed with saturated bicarbonate then brine. The organics were dried over sodium sulfate, filtered and concentrated to give 4.42 grams of a solid. This solid was suspended in 65 ml of ethanol and 14.3 mL of 1N sodium hydroxide was added. The reaction mixture was heated to 50° C. and stirred for 6.5 hours. The pH was adjusted to 3.0 with 1N phosphoric acid and extracted with methylene chloride. The organic layer was dried over sodium sulfate, filtered and concentrated in vacuo to give 3.82 grams (97% yield) of a solid.

Lithium hydroxide (1.26 grams, 30.12 mmol) was added to a stirring solution of the amidine (6.0 grams, 15.06 mmol) in tetrahydrofuran/water. The reaction was stirred at 75° C. for 2 hours and worked up by washing with ether. The aqueous layer was acidified to a pH of 4.5 with phosphoric acid and extracted with methylene chloride. Upon acidification, salts formed and were filtered before extraction. Organics from aqueous extraction were dried over sodium sulfate, filtered and concentrated in vacuo to yield 3.60 grams of a yellow solid (64.6%).

A solution of 2.00 grams (6.62 mmol) of this solid in 23 ml of N,N-dimethylformamide was added to a solution of 3.7 ml (26.6 mmol) of triethylamine and 647 mg (6.63mmol) of N,O-dimethylhydroxylamine hydrochloride in 33 ml of anhydrous N,N-dimethylformamide. To this solution was added 1.50 ml (9.93 mmol) of diethyl pyrocarbonate. The reaction was stirred at room temperature for 20 minutes then diluted with methylene chloride and washed with saturated bicarbonate. The organic layer was concentrated in vacuo to give an oil which was purified via flash silica gel chromatography eluting with 9% acetone in hexanes to give 1.15 grams (50%) of a solid. This solid was subsequenttly treated with 50 ml of a 1:1 ratio solution of trifluoroacetic acid in methylene chloride for 1.5 hours. The material was concentrated in vacuo and partitioned between 0.1 N sodium hydroxide and methylene chloride. The organic layer was dried over sodium sulfate filtered and concentrated to give 750 mg (92%) of a solid.

630mg (2.57 mmol) of weinreb's amide compound was dissolved in 26 ml of anhydrous tetrahydrofuran under nitrogen. The solution was cooled to −78° C. and (2.5 M, 7.75 mmol, 3.1 ml ) butyl lithium was added to the reaction mixture. After 10 minutes, the reaction was allowed to warm to room temperature. After 45 minutes the reaction mixture was quenched with 10 ml of 2N hydrochloric acid and stirred for an additional ½ hour. The mixture was partitioned between saturated bicarbonate solution and methylene chloride. The product was extracted from organic into 0.1 N hydrochloric acid. The aqueous layer was then basified to pH of 10 with 1N sodium hydroxide and subsequently extracted into methylene chloride, dried over sodium sulfate, filtered and concentrated in vacuo to give an orange solid. The solid was recrystallised from methanol to give 139 mg (22.3%) of a yellow solid. $^1$H NMR (250 MHz, CDCl₃) d 7.69 (s, 1H), 7.40 (m, 2H), 7.25 (d, J=8.2 Hz, 1H), 7.09 (m, 1H), 5.02 (br s, 1H), 2.90 (s, 2H), 2.87 (t, J=7.7 Hz, 12H), 1.69 (m, 2H), 1.40 (m, 2H), 0.964 (t, J=7.3 Hz, 3H); $^{13}$C NMR (75.5 MHz, CDCl$_3$) d 154.1, 149.0, 138.0, 132.0, 131.4, 129.8, 127.2, 126.9, 121.5, 36.85, 29.21, 27.08, 22.51, 13.93; HRMS calcd 242.14190, found 242.14194.

The title compounds of examples 12–15 were prepared analogously to the title compound described in Example 11 using the the appropriate reagent indicated.

EXAMPLE 12

1-(2-Amino-3H-benzo[b]azepin-4-yl)-butan-1-one

Propyl lithium. $^1$H NMR (250 MHz, CDCl$_3$) d 7.69 (s, 1H), 7.40 (m, 2H), 7.25 (d, J=7.9 Hz, 1H), 7.10 (d, J=7.4 Hz, 1H), 5.05 (brs, 2H), 2.91 (s, 2H), 2.86 (t, J=7.4 Hz, 2H), 1.75 (m, 2H), 1.00 (t, J=7.4 Hz, 3H); Mass spectrum FAB MH+ 229.

EXAMPLE 13

1-(2-Amino-3H-benzo[b]azepin-4-yl)-pentan-1-one

N-butyl lithium. $^1$H NMR (300 MHz, CDCl$_3$) d 7.67 (s, 1H), 7.39 (m, 2H), 7.24 (d, J=9.9 Hz, 1H), 7.08 (m, 1H), 5.01 (brs, 2H), 2.90 (s, 2H), 2.85 (t, J=7.4 Hz, 2H), 1.68 (m, 2H), 1.37 (m, 2H), 0.96 (t, J=7.4 Hz, 3H); HRMS calcd 242.14190; found 242.14194.

EXAMPLE 14

1-(2-Amino-3H-benzo[b]azepin-4-yl)-propan-1-one

Ethyl lithium. $^1$H NMR (250 MHz, CHCl$_3$) d 7.73 (s,1H), 7.35–7.51 (m, 3H), 7.22 (m, 1H), 3.12 (s, 2H), 2.92 (q, J=7.4Hz, 2H), 1.21 (t, J=7.4Hz, 3H); HRMS calcd 214.11060; found 214.11063.

EXAMPLE 15

(2-Amino-3H-benzo [b]azepin-4-yl)-phenyl-methanone

Phenyl lithium. $^1$H NMR (300 MHz, CDCl$_3$) d 7.75 (d, J=8.5 Hz, 2H), 7.22–7.61 (m, 7H), 7.06 (t, J=7.3 Hz, 1H), 5.21 (brs, 2H), 3.07 (s, 2H); HRMS Calcd 262.11060; found 262.10926.

EXAMPLE 16

2-Amino-3H-benzo[b]azepine-4-carboxylic Acid Dipropylamide

Diethyl pyrocarbonate (0.767 grams, 4.27 mmol) was added to a stirring solution of the acid (1.585 grams, 4.27 mmol), dipropyl amine (0.476 grams, 4.70 mmol), triethylamine (0.907 grams, 8.96 mmol) in methylene chloride. The reaction was stirred at room temperature for 7 hours, and worked up by partitioning between methylene chloride and saturated bicarbonate solution. Organics dried over sodium sulfate, filtered and concentrated to yield a brown oil. This oil was purified via silica gel column chromatography using a 4:1 ratio of hexanes:ethylacetate as eluent. 0.756 grams of a yellow foamy solid was obtained (39.1%).

The solid obtained was dissolved in 10 ml of a 1:1 ratio methylene chloride:trifluoroacetic acid solution and stirred at room temperature for three hours. The solution was then diluted with 200 ml of a 1:1 solution of methylene chloride and water. The aqueous layer was basified to a pH greater than 9 with anhydrous K$_2$CO$_3$, the layers were separated and the organic layer was washed with saturated sodium bicarbonate and brine. The organic layer was dried over sodium sulfate and concentrated in vacuo. The residue was purified via silica gel flash chromatography eluting with 3% methanol in chloroform to give 100 mg (23%) of an orange solid. $^1$H NMR (300 MHz, CDCl$_3$) d 7.85 (s 1H), d 7.50 (s 1H), d 7.35 (m 2H), d 6.85 (s 1H), d 4.05 (m 2H), d 3.30–3.50 (m 6H), d 3.20 (s 2H), d 1.25 (m 12H) mass spectrum MH+ 357.

The title compounds of examples 17–27 were prepared analogously to the title compound described in Example 16 using the the appropriate reagent(s) indicated.

EXAMPLE 17

2-Amino-3H-benzo[b]azepine-4-carboxylic Acid Diethylamide

Diethylamine. $^1$H NMR (250 MHz, CDCl$_3$) d 7.19–7.33 (m, 3H), 7.02 (dt, J=1.4, 6.8 Hz, 1H), 6.81 (s, 1H), 5.42 (brs, 2H), 3.52 (q, J=7.1 Hz, 4H), 2.78 (s, 2H), 1.22 (t, J=7.1 Hz, 6H); HRMS calcd 232.08478; found 232.08493

EXAMPLE 18

2-Amino-7-methoxy-3H-benzo[b]azepine-4-carboxylic Acid Pentylamide 8-methoxy-3H-benzo[b]azepine)-4-carboxylic acid; n-pentyamine. $^1$H NMR (250 MHz, CD$_3$OD) d 7.20 (s, 1H), 7.01 (d, J=8.9 Hz, 1H), 6.84 (dd, J=2.9, 8.9Hz, 1H), 6.71 (d, J=2.9 Hz, 1H), 3.89 (brs, 3H), 3.71 (s, 3), 3.24 (m, 2H), 2.76 (s, 2H), 1.49 (m, 2H), 1.21–1.27(m, 4H), 0.81 (m, 3H); HRMS calcd 301.17901 found 301.17835.

EXAMPLE 19

2-Amino-3H-baazepine-4-carboxylic Acid Dipropylamide

Dipropylamine. $^1$H NMR (250 MHz, CDCl$_3$) d 7.23–7.29 (m, 3H), 7.03 (dt, J=1.2, 6.8 Hz, 1H), 6.78 (s, 1H), 5.10 (brs, 2H), 3.43 (m, 4H), 2.75 (s, 2H), 1.64 (m, 4H), 0.90 (t, J=7.3 Hz, 6H); $^{13}$C NMR (75.5 MHz, CDCl$_3$) d 171.0, 154.1, 147.0, 130.6, 129.6, 128.4, 127.3, 126.8, 121.4, 34.08, 21.61, 11.32; HRMS calcd 285.18410; found 285.18431.

EXAMPLE 20

(2-Amino-3H-benzo[b]azepin-4-yl)-piperidin-1-vl-methanone

Piperidine. $^1$H NMR (300 MHz, CDCl$_3$) d 7.19–7.32 (m, 3H), 7.02 (m, 1 H), 6.79 (s, 1H), 5.09 (brs, 2H), 3.64 (m, 4H), 2.76 (s, 2H), 1.58–1.75 (m, 6H); $^{13}$C NMR (75.5 MHz, CDCl$_3$) d 169.5, 154.3, 147.2, 130.7, 130.5, 128.5, 127.7, 127.2, 126.8, 121.4, 33.90, 26.22, 24.67; HRMS calcd 269.15280; found 269.15291.

EXAMPLE 21

(2-Amino-3H-benzo[b]azepin-4-yl)-pyrrolidin-1-yl-methanone

Pyrrolidine. $^1$H NMR (300 MHZ, CDCl$_3$) d 7.16–7.30 (m, 3H),6.96–7.01 (m, 2H), 5.64 (brs, 2H), 3.67 (m, 2H), 3.53 (m, 2H), 2.81 (s, 2H), 1.90 (m, 4H); $^{13}$C NMR (75.5 MHz, CDCl$_3$) d 168.3, 154.7, 147.7, 131.7, 130.7, 128.9, 128.6, 127.3, 126.8, 121.2, 49.91, 46.46, 33.29, 26.55, 24.32; HRMS calcd 255.13715; found 255.13597.

EXAMPLE 22

2-Amino-3H-benzo[b]azepine-4-carboxylic Acid Dibutylamide

Dibutylamine. $^1$H NMR (250 MHZ, CDCl$_3$) d 7.21–7.35 (m, 3H), 7.04 (m, 1H), 6.80 (s, 1H), 5.17 (brs, 2H), 3.48 (m, 4H), 2.75 (s, 2H), 1.61 (m, 4H), 1.35 (m, 4H), 0.94 (t, J=7.2 Hz, 6H); $^{13}$C NMR (75.5 MHz, CDCl$_3$) d 170.8, 154.4, 147.4, 130.4, 129.5, 128.3, 128.2, 127.1, 126.6, 33.94, 29.52, 15.10, 13.68; HRMS calcd 313.21540 found 313.21475.

EXAMPLE 23

2-Amino-8-trifluoromethyl-3H-benzo[b]azepine-4-carboxylic Acid Dipropylamide 8-trifluoromethyl-3H-benzo[b]azepine-4-carboxylic acid. $^1$H NMR (250 MHz, CDCl$_3$) d 7.59 (s, 1H), 7.38 (m, 2H), 6.81 (s, 1H), 3.40 (m, 4H), 3.02 (s, 2 H), 1.63 (m, 4H), 0.90 (m, 6H); $^3$C NMR (75.5 MHz, CDCl$_3$) d 177.9, 169.8, 160.6, 141.7, 139.7, 131.38, 131.2, 131.1, 130.8, 130.4, 129.0, 125.4, 122.4, 122.3, 121.8, 119.7, 60.06, 33.70, 22.54, 11.28; HRMS calcd 353.1715 found 353.17024.

EXAMPLE 24

2-Amino-8-methoxy-3H-benzo[b]azepine-4-carboxylic Acid Dipropylamide 8-methoxy-3H-benzo[b]azepine-4-carboxylic acid. $^1$H NMR (250 MHz, CDCl$_3$) d 7.17 (dd, J=8.6 Hz, 1H), 6.75 (m, 2H), 6.66 (dd, J=2.6, 8.6 Hz, 1H), 3.83 (s, 3H), 3.44 (m, 4H), 2.79 (s, 2H), 1.64 (m, 4H), 0.91 (t, J=7.4 Hz, 6H); $^{13}$C NMR (75.5 MHz, CDCl$_3$) d 171.2, 159.8, 154.3, 147.9, 131.8, 129.7, 125.6, 120.5, 110.7, 109.0, 55.31, 34.02, 21.57, 11.33 HRMS calcd 315.1914 found 315.1938.

EXAMPLE 25

2-Amino-8-trifluoromethyl-3H-benzo[b]azepine-4-carboxylic Acid Diethylamide

Diethylamine. $^1$H NMR (250 MHz, CDCl$_3$) d 7.41 (d, J=1.5 Hz, 1H), 7.26 (d, J=8.2 Hz, 1H), 7.17 (dd, J=1.5, 8.2 Hz, 1H), 6.72 (s, 1H), 3.49 (q, J=7.1 Hz, 4H), 2.80 (s, 2H), 1.22 (t, J=7.1 Hz, 6H); $^{13}$C NMR (75.5 MHz, CDCl$_3$) d 170.2, 155.4, 147.3, 131.3, 130.8, 130.0, 128.3, 125.9, 123.9, 122.9, 117.0, 34.10; HRMS calcd 326.14802 found 326.14771.

EXAMPLE 26

2-Amino-8-rifluoromethyl-3H-benzo[b]azepine-4-carboxylic Acid Dimethylamide

Dimethylamine. $^1$H NMR (250 MHZ, CDCl$_3$) d 7.50 (s, 1H), 7.39 (d, J=8.1 Hz, 1H), 7.22 (d, J=8.1 Hz, 1H), 6.80 (s, 1H), 3.39 (brs, 6H), 2.82 (s, 2H); mass spectrum MH+ 298.

EXAMPLE 27

2-Amino-3H-benzo[b]azepine-4-carboxylic Acid Pentylamide

N-pentylamine. $^1$H NMR (300 MHz, dimethyl sulfoxide) d 8.33 (m, 1H), 7.21–7.49 (m, 5H), 3.10 (m, 2H), 1.41 (m, 2H), 1.20 (m, 4H), 0.79 (m, 3H); masspectrum MH+ 272.

What is claimed is:

1. A compound of Formula (Ia):

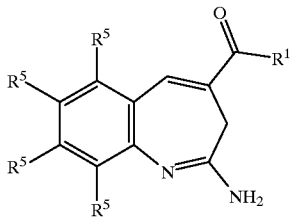

(Ia)

or a pharmaceutically acceptable salt thereof; wherein:

$R^1$ is selected from the group consisting of hydrogen; hydroxy; (C$_1$–C$_6$) alkoxy; (C$_1$–C$_6$) alkyl; (C$_6$–C$_{10}$) aryl; or NR$^{17}$R$^{18}$, where:

$R^{17}$ and $R^{18}$ are each independently hydrogen; (C$_1$–C$_6$) alkyl; or (C$_8$–C$_{10}$) aryl; and is independently selected from the group consisting of hydrogen; (C$_1$–C$_6$) alkyl optionally substituted by (C$_1$–C$_6$) alkylthio, (C$_1$–C$_6$) alkoxy, (C$_6$–C$_{10}$) aryl, hydroxy(C$_1$–C$_6$) alkyl, (C$_1$–C$_6$) acylamino, (C$_1$–C$_6$) alkylsulfinyl, (C$_1$–C$_6$) alkylsulfonyl, amino, (C$_1$–C$_6$) alkylamino, or ((C$_1$–C$_6$) alkyl)$_2$ amino; halo; cyano; amino; hydroxy; (C$_2$–C$_6$) alkenyl; (C$_2$–C$_6$) alkynyl; (C$_1$–C$_6$) alkylamino; ((C$_1$–C$_6$) alkyl)$_2$ amino; (C$_1$–C$_6$) alkylsulfonamido; aminosulfonyl; (C$_1$–C$_6$) alkylaminosulfonyl; ((C$_1$–C$_6$) alkyl)$_2$ aminosulfonyl; (C$_1$–C$_6$) alkylthio; (C$_1$–C$_6$) alkoxy; (C$_6$–C$_{10}$) aryl; (C$_3$–C$_6$) cycloalkyl; (C$_1$–C$_6$) acylamino; and a group of the formula:

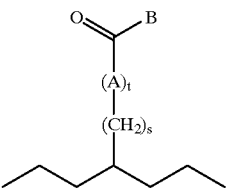

wherein:
s is 0 to 6;
t is 0 or 1;
A is oxygen or NH; and
B is hydroxy; (C$_1$–C$_6$) alkoxy; or NR$^7$R$^8$ where:
$R^7$ and $R^8$ are each independently hydrogen; or (C$_1$–C$_6$) alkyl.

2. A compound according to claim 1, wherein each $R^5$ is independently selected from the group consisting of hydrogen, halo, cyano, hydroxy, ((C$_1$–C$_6$)alkyl)$_2$amino, and a group of the formula

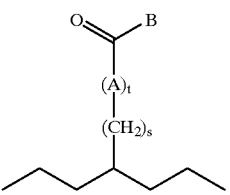

wherein s is 0; t is 0; and B is (C$_1$–C$_6$)alkoxy or NR$^7$R$^8$ wherein $R^7$ and $R^8$ are each (C$_1$–C$_6$)alkyl.

3. A compound according to claim 1, selected from the group consisting of;

2-Amino-8-hydroxy-9-methoxy-3H-benzo[b]azepine-4-carboxylic acid ethyl ester;
2-Amino-9-methoxy-3H-benzo[b]azepine-4-carboxylic acid ethyl ester;
2-Amino-7-hydroxy-8-methoxy-3H-benzo[b]azepine-4-carboxylic acid ethyl ester;
2-Amino-6-methoxy-3H-benzo[b]azepine-4-carboxylic acid ethyl ester;
2-Amino-8-hydroxy-7-methoxy-3H-benzo[b]azepine-4-carboxylic acid ethyl ester;
2-Amino-3H-benzo[b]azepine-4-carbaldehyde.

4. A pharmaceutical composition for the treatment of myelosuppression associated with cancer chemotherapy and activation of the immune system for the treatment of cancer in a mammal including a human, comprising an amount of a compound of claim 1 or a pharmaceutically acceptable salt thereof, effective in such treatments, and a pharmaceutically acceptable carrier.

5. A method for the treatment of myelosuppression associated with cancer chemotherapy and activation of the immune system for the treatment of cancer in a mammal including a human, comprising administering to said mammal an amount of a compound of claim 1 or a pharmaceutically acceptable salt thereof effective is such treatments.

* * * * *